United States Patent [19]

Horan et al.

[11] Patent Number: 4,743,594
[45] Date of Patent: May 10, 1988

[54] ANTIBIOTIC, ANTITUMOR COMPOUNDS AND THEIR USE

[75] Inventors: Ann C. Horan, Summit, N.J.; Jerzy Golik, Syracuse; James A. Matson, Fayetteville, both of N.Y.; Mahesh G. Patel, Verona, N.J.

[73] Assignee: Schering Corporation, Kenilworth, N.J.

[21] Appl. No.: 651,498

[22] Filed: Sep. 17, 1984

[51] Int. Cl.$^4$ ............... A61K 31/71; C07H 17/00; C12P 19/28
[52] U.S. Cl. ..................... 514/43; 514/42; 536/22; 536/23; 536/24; 536/18.1; 435/119
[58] Field of Search .............. 514/42, 43; 536/22, 536/24, 18.1, 23

[56] References Cited

U.S. PATENT DOCUMENTS

| | | | |
|---|---|---|---|
| 4,487,925 | 12/1984 | Nettleton et al. | 536/24 |
| 4,524,145 | 6/1985 | Matson | 514/43 |

FOREIGN PATENT DOCUMENTS

| | | | |
|---|---|---|---|
| 115350 | 8/1984 | European Pat. Off. | 536/24 |
| 18035 | 4/1984 | Japan . | |

Primary Examiner—J. R. Brown
Assistant Examiner—Elli Peselev
Attorney, Agent, or Firm—Thomas D. Hoffman; Gerald S. Rosen

[57] ABSTRACT

Actinomadura melliaura nov. sp. (ATCC 39691) produces four novel compounds which we have designated AT 2433 $A_1$, AT 2433 $A_2$, AT 2433 $B_1$ and AT 2433 $B_2$. The novel compounds or pharmaceutically acceptable salts thereof exhibit antibacterial and antitumor activity.

13 Claims, No Drawings

ND THEIR USE

ANTIBIOTIC, ANTITUMOR COMPOUNDS AND THEIR USE

BACKGROUND OF THE INVENTION

This invention relates to a novel microorganism and to the novel compositions of matter produced therefrom. More particularly, this invention relates to a novel antibiotic AT 2433 complex produced by fermentation under controlled conditions using a biologically pure culture of a new microorganism *Actinomadura melliaura* sp. nov., a species of the genus Actinomadura. This invention also relates to the use of antibiotic complex AT 2433 and the four components thereof as antibacterial agents and to their use as antitumor agents.

SUMMARY OF THE INVENTION

This invention provides a compound represented by the formula 1:

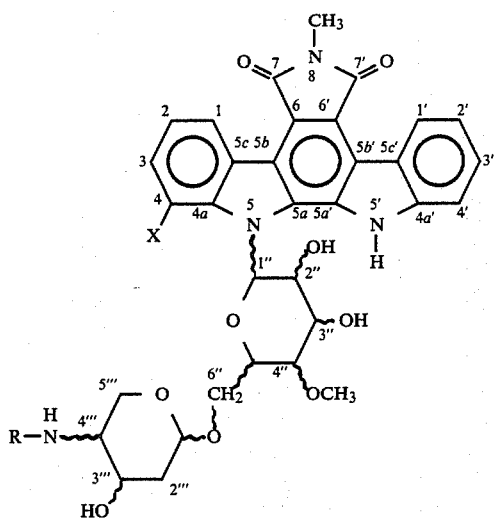

wherein X is H or Cl; and R is H or $CH_3$; or a pharmaceutically acceptable salt thereof; in racemic or optically active form.

The wavey lines represent bonds to the two six-membered sugar rings and signify that the substituents attached to each sugar ring may be in any of the possible stereochemical configurations. The conformation of each sugar ring may be the chair and/or boat form(s).

Antibiotic AT 2433 is a complex of four components, each of which is represented by the formula 1. The complex of the four components is designated herein as "antibiotic AT 2433 complex". Individually, the four AT 2433 components are designated AT 2433 $A_1$, $A_2$, $B_1$ and $B_2$ and are specified by reference to the formula 1 hereinabove and the Table I hereinbelow.

TABLE I

| AT 2433 Component | X | R |
|---|---|---|
| $A_1$ | Cl | $CH_3$ |
| $A_2$ | Cl | H |
| $B_1$ | H | $CH_3$ |
| $B_2$ | H | H |

This invention also provides a process for producing antibiotic AT 2433 complex which comprises cultivating a strain of *Actinomadura melliaura* sp. nov., capable of producing antibiotic AT 2433 complex in an aqueous nutrient medium containing assimilable sources of carbon and nitrogen under submerged aerobic conditions until an amount of antibiotic AT 2433 complex is produced by said strain in said nutrient medium. The antibiotic AT 2433 complex is recovered and separated into its four components designated antibiotics AT 2433 $A_1$, $A_2$, $B_1$ and $B_2$.

The preferred culture for producing a compound of formula 1 and the antibiotic AT 2433 complex is a biologically pure culture of the microorganism *Actinomadura melliaura* having the identifying characteristics of ATCC 39691.

Antibiotic AT 2433 complex and the four components isolated therefrom are effective against various gram-positive and gram-negative bacteria and exhibit activity against experimental animal tumor systems, e.g., P-388 leukemia in mice.

This invention also provides a pharmaceutical composition comprising a compound represented by formula 1, hereinabove, wherein X is H or Cl and wherein $R_1$ is H or $CH_3$ or a pharmaceutically acceptable salt thereof, in racemic or optically active form and an inert pharmaceutically acceptable carrier or diluent.

In another aspect of this invention, there is provided a method of treating a mammalian host affected by a malignant tumor, which comprises administering to said host having a malignant tumor a therapeutically effective amount of a compound represented by formula 1 or a pharmaceutical composition thereof.

In another aspect of this invention there is provided a method of treating susceptible bacterial infections which comprises administering to a host in need of such treatment a compound of formula 1 or a pharmaceutical composition thereof in an amount sufficient to treat such infection.

DETAILED DESCRIPTION OF THE INVENTION AND OF THE PREFERRED EMBODIMENTS

The Microorganism

The antibiotic AT 2433 complex represented by the formula 1 is produced by fermentation of a biologically pure culture of *Actinomadura melliaura* sp. nov., designated as strain SCC 1655. *Actinomadura melliaura* SC1655 was obtained from a soil sample collected in Bristol Cove, Calif.

A subculture of this microorganism has been made a part of the permanent collection of the American Type Culture Collection, Rockville, Md., and it has been assigned accession number ATCC 39691 in the depository. While the microorganism is available to the public without restriction, use of the microorganism is dependent on the U.S. Patent Laws.

DESCRIPTION OF THE PRODUCING STRAIN

*Actinomadura melliaura* sp. nov. ATCC 39691

The taxonomic methods used herein were those cited by Gordon [Gordon, R. E., "Some criteria for the recognition of *Norcardia madurae* (Vincent) Blanchard" *J. Gen. Microbiol.*, 45: 355–364, 1966], and by Leudemann and Brodsky [Leudemann, G. M., and Brodsky, B., "*Micromonospora carbonacea* sp. nov., and Everninomicin-producing organism", Antimicrob. Agents Chemother., p. 47–52, 1964], and by Horan and Brodsky [Horan, A. C., and B. C. Brodsky, "A novel antibiotic-producing Actinomadura, *Actinomadura kijaniata* sp.

nov.", *Int. J. Syst. Bacteriol.*, 32: 195-200, 1982], and by Becker et al. [Becker, B., Lechevalier, M. P., and Lechevalier, H. A., "Chemical composition of cell wall preparations from strains of various genera or aerobic actinomycetes", *Appl. Microbiol.*, 13; 236-243, 1966], and by Lechevalier and Lechevalier, [Lechevalier, M. P. and Lechevalier, H. A., "Chemical composition as a criteria in the classification of aerobic actinomycetes", *Int. J. Syst. Bacteriol* .20: 487-493, 1970], and by Shirling and Gottlieb [Shirling, E. B., and D. Gottlieb, "Methods for characterization of Streptomyces species", *Int. J. Syst. Bacteriol.*, 16: 313-340, 1966], and by Waksman [Waksman, S. A., "The Actinomycetales", Vol. 2, The Williams and Wilkins Co., Baltimore, Md.].

MACROSCOPIC CHARACTERISTICS of *Actinomadura melliaura* ATCC 39691

After 14 to 21 days at 30° C., good growth of *Actinomadura melliaura* ATCC 39691 occurs on Emerson's NZA-glucose, yeast extract-glucose, ISP 2, 6, and 7 agars. On most other media, growth is fair. Diffusible pigments are not formed on the media tested. Aerial mycelia, white in mass, are formed on Czapek-sucrose, yeast extract-glucose, ISP-3, and 4 agars. Vegetative mycelial pigments range form tan to gold to brown. Colors used in description of pigments follow color-name charts in Color Harmony Manual, 4th ed., Container Corp. of America, Chicago, 1958; and in Descriptive Color Names Dictionary, Container Corp. of America, Chicago, 1950, Taylor H. D., Knoche, L., and Granville, W. C. Culture characteristics are presented in Table II.

MICROSCOPIC CHARACTERISTICS of *Actinomadura melliaura* ATCC 3961

On water agar after 10 to 14 days at 30° C. abundant, fine (0.5 to 0.8 microns in diameter), aerial mycelia are formed. Long sporophores with straight or slightly hooked chains of 10-20 spores occur along the length of the aerial mycelia. Characteristically at the terminal ends of the aerial mycelia, two sporophores bearing spores can be observed. Spores are cylindrical, non-motile, 1.0 to 2.0 microns in diameter and appear smooth-walled.

PHYSIOLOGICAL CHARACTERISTICS of *Actinomadura melliaura* ATCC 39691

Growth for *Actinomadura melliaura* ATCC 39691 occurs at temperatures in the range of about 27° C. to 40° C. on yeast extract-glucose agar. The optimum growth temperature range is about 30° C. to 35° C. Poor growth was observed at about 10° C. and 45° C. Other physiological properties for the strain are shown in Table III. *Actinomadura melliaura* ATCC 39691 utilizes most sugars and a range of organic acids for growth. The carbon utilization results are summarized in Table IV.

TABLE II

Macroscopic Appearance of *Actinomadura melliaura* ATCC 39691 Grown on Various Descriptive Media.

| MEDIUM | DESCRIPTION |
|---|---|
| Bennett's Agar | G: +, fair |
| | S: flat, granular |
| | AM: absent |
| | DFP: absent |
| | C: g 2 gc, bamboo |
| Czapek Sucrose Agar | G: ± to +, poor to fair |
| | S: flat, smooth |
| | AM: present, white |
| | DFP: absent |
| | C: g 2 gc, bamboo |
| Glucose Asparagine Agar | G: +, fair |
| | S: flat, granular |
| | AM: absent |
| | DFP: absent |
| | C: g 2 ea, light wheat |
| Glycol Asparagine Agar | G: ++, moderate |
| | S: raised, granular |
| | AM: absent |
| | DFP: absent |
| | C: g 2 le, mustard |
| Nutrient Agar | G: +, fair |
| | S: flat, folded to ridged |
| | AM: absent |
| | DFP: absent |
| | C: g 2 ic, honey gold |
| Peptone Glucose Agar | G: ± to +, poor to fair |
| | S: slightly raised, folded |
| | AM: absent |
| | DFP: absent |
| | C: g 2 gc, bamboo |
| Potato Dextrose Agar | G: ++, moderate |
| | S: raised, folded |
| | AM: absent |
| | DFP: absent |
| | C: g 3 lg, adobe brown |
| Emerson's Agar | G: +++, good |
| | S: raised, folded |
| | AM: absent |
| | DFP: absent |
| | C: g 2 ic, honey gold |
| NZA Glucose Agar | G: +++, good |
| | S: raised, folded |
| | AM: absent |
| | DFP: absent |
| | C: g 3 le, yellow maple |
| Yeast Extract Glucose Agar | G: +++, good |
| | S: raised, folded |
| | AM: present, white |
| | DFP: absent |
| | C: g 3 le, yellow maple |
| Tomato Paste Oatmeal Agar | G: ++, moderate |
| | S: flat, slightly folded |
| | AM: absent |
| | DFP: absent |
| | C: g 3 ie, camel |
| Yeast Extract Malt Extract Agar (ISP #2) | G: +++, good |
| | S: raised, folded |
| | AM: absent |
| | DFP: absent |
| | C: g 3 le, yellow maple |
| Oatmeal Agar (ISP #3) | G: +, fair |
| | S: flat, smooth |
| | AM: present, white |
| | DFP: absent |
| | C: g 2 ic, honey gold |
| Inorganic Salts-Starch Agar (ISP #4) | G: +, fair |
| | S: flat to granular |
| | AM: present, white |
| | DFP: absent |
| | C: g 2 ic, honey gold |
| Starch Agar (Waksman #21) | G: +, fair |
| | S: flat to slightly raised |
| | AM: absent |
| | DFP: absent |
| | C: g 2 ic, honey gold |
| Calcium Maleate Agar (Waksman #7) | G: +, fair |
| | S: flat to slightly raised |
| | AM: absent |
| | DFP: absent |
| | C: g 2 ic, honey gold |
| Peptone Iron Agar (ISP #6) | G: +++, good |
| | S: raised, folded |
| | AM: absent |
| | DFP: present, amber |
| | C: g 3 ie, camel |

TABLE II-continued
Macroscopic Appearance of *Actinomadura melliaura* ATCC 39691 Grown on Various Descriptive Media.

| MEDIUM | DESCRIPTION |
|---|---|
| Tyrosine Agar (ISP #7) | G: +++, good |
|  | S: raised, folded |
|  | AM: present, white |
|  | DFP: absent |
|  | C: g 3 lg, adobe brown |
| Starch Agar (Gordon) | G: ++, moderate |
|  | S: raised, folded |
|  | AM: absent |
|  | DFP: absent |
|  | C: g 2 ec, ecru |

G, growth; S, surface characteristics; AM, aerial mycelia; DFP, diffusible pigments; C, color.

TABLE II
Physiological properties of *Actinomadura melliaura* ATCC 39691

| TEST | Result |
|---|---|
| Hydrolysis of: | |
| Adenine | + |
| Hypoxanthine | + |
| Tyrosine | + |
| Xanthine | − |
| Casein | − |
| Gelatin | + |
| Hippurate | + |
| Xylan | + |
| Starch | + |
| Breakdown of: | |
| Urea | − |
| Allantoin | − |
| Loeffler's Serum | +, slight |
| Dorsett's Egg | − |
| Formation of: | |
| Melanin | − |
| H$_2$S | − |
| Nitrate to Nitrite | + |
| Growth in the Presence of 50 mcg/mL of: | |
| Gentamicin | + |
| Sisomicin | + |
| Neomycin | + |
| Kanamycin | + |
| Streptomycin | + |
| Paromomycin | + |
| Spectinomycin | + |
| Rosaramicin | + |
| Everninomicin | − |
| Rifamycin | − |
| Penicillin G | + |
| Cephalothin | + |
| Lincomycin | + |
| Tetracycline | + |
| Growth in the presence of: NaCl | |
| 1% | +++, good |
| 2% | +, poor to fair |
| 3% | ±, poor |
| Sensitivity to: | |
| Lysozome | + |
| Salicylate | + |

TABLE IV
Carbon Utilization for *Actinomadura melliaura* ATCC 39691

| TEST | Result | |
|---|---|---|
| Carbohydrate Utilization[1] | | |
| Adonitol | +++, | good |
| D-Arabinose | +++, | good |
| L-Arabinose | +++, | good |
| Cellibiose | +++, | good |
| Dextrin | +++, | good |
| Dulcitol | ±, | poor |
| Erythritol | ±, | poor |
| Fructose | +++, | good |
| L-Fucose | +++, | good |
| Galactose | +++, | good |
| Glucose | +++, | good |
| α-m-d-glucoside | ±, | poor |
| m-β-D-glucopyranoside | +++, | good |
| Glycerol | +++, | good |
| Inositol | +++, | good |
| Inulin | ++, | moderate |
| Lactose | ±, | poor |
| Maltose | +++, | good |
| Mannitol | +++, | good |
| Mannose | +++, | good |
| Melibiose | ±, | poor |
| Melizitose | ±, | poor |
| Raffinose | ±, | poor |
| Rhamnose | +++, | good |
| Ribose | +++, | good |
| Sucrose | ±, | poor |
| Trehalose | +++, | good |
| D-xylose | +++, | good |
| Organic Acid Utilization[2] | | |
| Acetate | + | |
| Benzoate | − | |
| Citrate | + | |
| Formate | − | |
| Glutamate | + | |
| Lactate | + | |
| Maleate | + | |
| Oleate | − | |
| Oxalate | − | |
| Propionate | + | |
| Succinate | + | |
| Tartrate | − | |
| Pyruvate | + | |

[1]Medium of Leudemann & Brodsky (Antimicrob. Agents Chemother. p 47-52, 1964).
[2]Medium of Gordon (J. Gen. Microbiol. 45: 355-364, 1966.)

Cell Wall Amino Acid and Whole Cell Sugar Components

The cell wall of *Actinomadura melliaura* ATCC 39691 was examined according to the methods described by Becker et al. (*Appl. Microbiol.* 13; 236-243, 1965) and Yamaguchi (*J. Bacteriol.* 89: 441-453, 1965) and found to contain the amino acid meso-diaminopimelic acid. The characteristic sugar component in the whole cell hydrolyzate was identified as Madurose (3-O-methyl-D galactose) according to the procedures outlined by Lechevalier and Lechevalier in *Biology of the Actinomycetes and Related Organisms* 11: 78-92, 1976.

Based on cell wall analysis and morphologic characteristics, the culture is catagorized as a species of the genus Actinomadura, designated *Actinomadura melliaura* ATCC 39691. The novel *Actinomadura melliaura* ATCC 39691 was compared with thirteen deposited species of the Actinomadura genus. Of the thirteen deposited strains, *Actinomadura melliaura* ATCC 39691 shares vegetative mycelial pigmentation with *A. helvata, A. flava,* and *A. brunnea; Actinomadura melliaura* ATCC 39691 differs from *A. helvata* in morphology of the spore chain, color of the aerial mycelia, utilization of methyl-β-D-glucoside, and in antibiotic production. *Actinomadura melliaura* ATCC 39691 differs from *A. flava* in aerial mycelia formation, morphology of the spore bearing hyphae where the entire aerial mycelia fragments into chains of spores, in utilization of methyl-β-D-glucoside, and in antibiotic production; and from *A. brunnea* in morphology, color of the aerial mycelia, utilization of methyl-β-D-glucoside and of mannitol, and in antibiotic activity. Table V compares *Actinomadura melliaura fulva* ATCC 39691 to the named strains of Actinomadura.

Based on the unique morphology of *Actinomadura melliaura* ATCC 39691 and its characteristic physiologic and cultural characteristics, as well as the production of the novel antibiotic AT 2433 complex, the culture is considered to represent a distinct, new species of the genus Actinomadura for which the name *Actinomadura melliaura* Horan and Brodsky sp. nov. (SCC 1655) is proposed, in accordance with the Rules of Nomenclature of Bacteria (Lapage, S. P., P. H. A. Sneath, E. F. Lessel, V. B. D. Skerman, H. P. R. SeeLiger, and W. A. Clark, ed. 1975, and International Code of Nomenclature of Bacteria, 1976 revision, American Society for Microbiology, Washington, D.C.) It is understood that should another strain of this new species of the genus Actinomadura be found, the type strain would also be the type subspecies.

The species name selected refers to the yellow-brown vegetative mycelial pigments formed.

TABLE V

Comparative Characteristics of Species of Actinomadura

| Taxon | spore chain | spore surface | aerial mycelia color | vegetative mycelia color |
|---|---|---|---|---|
| *Actinomadura melliaura* | straight open, short to long | smooth | white | tan to, yellow-brown |
| *A. citrea* ATCC 27887 | straight to hooked, short | uneven | yellow-blue | lemon-yellow |
| *A. flava* ATCC 29533 | fragmentation of entire aerial mycelia into chains of spores, straight, long | smooth | rarely formed | lemon-yellow/ yellow-brown |
| *A. helvata* ATCC 27295 | closed spirals, short | smooth | white to pink | yellow-brown |
| *A. kijaniata* ATCC 31588 | fragmentation of entire aerial mycelia ito chains of spores, flexous spirals, long | smooth | white to pale green | dark green |
| *A. macra* ATCC 31286 | straight to flexous, short | smooth | grayish | cream to gray |
| *A. madurae* ATCC 19425 | curls to hooks, short | smooth | rarely formed white to pink | pink to red |
| *A. malachitica* ATCC 27888 | loose spirals, short | smooth | rarely formed pale green | cream |
| *A. pelletieri* ATCC 14816 | curls to hooks, short | smooth | rarely formed white to pink | pink to red |
| *A. pusilla* ATCC 27296 | closed spirals, short | smooth | white to pink | brownish-gray/blue black |
| *A. roseoviolacea* ATCC 27297 | hooks to closed spirals, short | smooth-uneven | white to pink | red to violet |
| *A. rubra* ATCC 27031 | hooks to spirals, short | smooth-uneven | rarely formed white to pink | brick red |
| *A. spadix* ATCC 27298 | hooks to closed spirals, short | smooth | grayish | gray-brown |
| *A. verrucosospora* ATCC 27299 ATCC 31466 | hooks to spirals | uneven | grayish-blue | pink |

| Taxon | Meso-Diamino-Pimelic Acid and Madurose | Antibiotic Activity | Hydrolysis of Xanthine | Utilization of Methyl-β-D-Glucoside | Mannitol |
|---|---|---|---|---|---|
| *Actinomadura melliaura* ATCC 39691 | + | + | − | − | − |
| *A. citrea* ATCC 27887 | + | − | − | − | + |
| *A. flava* ATCC 29533 | + | + | − | − | + |
| *A. helvata* ATCC 27295 | + | − | − | − | + |
| *A. kijaniata* ATCC 31588 | + | + | + | + | − |
| *A. macra* ATCC 31286 | + | + | − | − | − |
| *A. madurae* ATCC 19425 | + | + | − | − | + |
| *A. malachitica* ATCC 27888 | + | − | − | − | + |
| *A. pelletieri* ATCC 14816 | + | + | − | − | − |
| *A. pusilla* ATCC 27296 | + | + | − | + | − |
| *A. roseoviolacea* | + | − | − | − | + |

TABLE V-continued

Comparative Characteristics of Species of Actinomadura

| | | | | | |
|---|---|---|---|---|---|
| ATCC 27297 | | | | | |
| A. rubra | + | + | − | − | + |
| ATCC 27031 | | | | | |
| A. spadix | + | − | − | − | + |
| ATCC 27298 | | | | | |
| A. verrucosospora | + | −, + | − | − | + |
| ATCC 27299 | | | | | |
| ATCC 31466 | | | | | |

It is to be understood that the present invention is not limited to use of the particular preferred strain *Actinomadura melliaura* ATCC 39691 described above or to organisms fully answering the above descriptions. It is especially intended to include other antibiotic AT 2433 complex-producing strains or mutants of the said organism which can be produced by conventional means such as x-radiation, ultraviolet radiation, treatment with nitrogen mustards, phage exposure, and the like.

FERMENTATION

*Actinomadura melliaura* ATCC 39691 when fermented under controlled conditions in a suitable medium, produces the antibiotic AT 2433 complex from which are isolated four compounds represented by formula 1 and designated as AT 2433 $A_1$, AT 2433 $A_2$, AT 233 $B_1$, and AT 2433 $B_2$.

The fermentation which produces the antibiotics is commenced by the production of a vigorous vegetative inoculum which is usually produced in two or three stages. A suitable media for preparing such inoculum is set forth herein below as Medium A and Medium B. The inoculum and the fermentation are conducted in a medium wherein the pH is maintained at from about 6.5 to about 8.5, preferably about 7.5 for the inoculum and 7.0 for the fermentation. The proper pH ranges are usually maintained by the incorporation of suitable buffers, such as calcium carbonate in the media.

The vegetative inoculum and the fermentation are effected at a temperature from about 27° C. to about 40° C. The preferred temperature range in which to prepare the vegetative inoculum and to conduct the fermentation is about 30° to 35° C.

In general, the nutrient media are prepared in a suitable fermentation vessel or flask, which is sterilized and cooled prior to inoculation. However, the media may be stored under aseptic conditions at sub-zero temperature prior to use.

Stock cultures of *Actinomadura melliaura* ATCC 39691 are maintained as frozen whole broths.

INOCULUM PREPARATION

In order to produce the antibiotic AT 2433 complex of this invention, a vigorously growing vegetative inoculum is preferred.

In general, inoculum preparation is carried out in two or more stages. For large scale fermentations (e.g. about 50 liters), it is preferred that the inoculum be prepared in three stages.

A suitable medium for preparing vegetative inocula are as follows:

| Medium A* | |
|---|---|
| Beef Extract | 3 g |
| Tryptose | 5 g |
| Cerelose | 1 g |
| Potato Starch | 24 g |
| Yeast Extract | 5 g |
| Calcium Carbonate | 2 g |
| Tap Water to | 1.0 liter |

*The pH is adjusted, if needed, to 7.5 with NaOH.

Two mL of freshly thawed whole broth of a 5 vol. % suspension of *Actinomadura melliaura* is used to inoculate 50 mL of sterile Medium A.

The flask is incubated at about 30° C. for from about 48 to about 96 hours, preferably about 72 hours on a shaker at about 300 rpm and having a 2 inch throw.

SECOND INOCULUM STAGE

A series of 2 L Erlenmeyer flasks containing 500 mL of sterile Medium A are inoculated with 25 mL of a 5 vol. % of the first inoculum. The incubation procedure described for the first inoculum stage is followed.

THIRD INOCULUM STAGE (Optional)

Twenty-five mL of the second inoculum is used to inoculate each of a series of 500 mL portions of sterile Medium B in two liter Erlenmeyer flasks. The flasks are incubated with agitation at about 350 rpm and at about 30° C. for from about 24 to about 72 hours, preferably about 48 hours. Aeration at about 0.35 volume of air/volume of fermentation/minute (VVM).

In one aspect of this invention the third inoculum stage is not performed. Antibiotic production is started using the second inoculum stage.

ANTIBIOTIC PRODUCTION (Fermentation)

The following medium designated Medium B has been found to provide both satisfactory and reproducible yields of antibiotic production:

| Medium B | |
|---|---|
| Yeast Extract | 5 9/liter |
| Cerelose | 10 g/liter |
| Soluble Starch | 20 g/liter |
| NZ Amine (Difco) | 5 g/liter |
| Calcium Carbonate | 4 g/liter |
| Cobalt (II) Chloride [c, $10^{-3}$ M] | 1 m/L |
| Tap Water to | 1 liter |
| Post-sterilization | pH 7.0 |

Inoculate ten liters of sterile Medium B with 500 mL of second inoculum stage prepared as described above. Incubate the fermentation mixture at from about 27° C. to above 40° C., preferably about 30° C. to about 35° C., with agitation and aeration at about 350 rpm and at 0.35 VVM, respectively. Maintain the pH of the fermentation at from about 6.8 to about 7.5 by the addition of dilute acid or alkali, if necessary. The addition of dilute acid or dilute alkali is usually unnecessary. However, in a normal fermentation, the pH will climb to about 7.5 and will drop back to neutrality by the end of the fermentation.

Production of the antibiotic AT 2433 was monitored by whole broth well assays against *Micrococus luteus* ATCC 9341 or *Staphylococcus aureus* 209 P in neomycin assay agar (BBL).

ISOLATION OF ANTIBIOTIC AT 2433 COMPLEX AND SEPARATION OF ANTIBIOTICS AT 2433 $A_1$, $A_2$, $B_1$ AND $B_2$

Antibiotic At 2433 complex is isolated from the broth by extraction using about two volumes of immiscible organic solvent, e.g., ethyl acetate per extract and by extracting the broth twice. The extracts are combined, evaporated to a residue and dissolved in a hydrocarbon solvent, e.g., Skellysolve B, and methanol. One part of water per ten volumes of methanol is added, and liquid-liquid partition of the antibiotic AT 2433 complex is employed. The aqueous methanol layer is separated and extracted with two portions of, for example, Skellysolve B. Additional water is added to form 1:3 (v/v) water:methanol which is extracted with 3 equal volumes of, for example, carbon tetrachloride. Additional water is added to form 1:2 (v/v) water:methanol which is extracted with 6 equal volumes of chloroform (or methylene chloride). The chloroform extracts are combined and evaporated to give a residue. The residue is subjected to medium pressure liquid chromatography on a silica gel column using as an eluant, the lower phase of 4:4:3, (v/v/v) solution of chloroform:methanol:water. Elution is commenced and the fractions containing AT 2433 $A_1$ and $A_2$ (as determined by similar $R_f$ values on silica gel tlc plates) are evaporated to give a mixture of AT 2433 $A_1$ and $A_2$. In a similar fashion, the fraction containing AT 2433 $B_1$ and $B_2$ are pooled and evaporated to give a mixture of AT 2433 $B_1$ and $B_2$. AT 2433 $A_1$ and $A_2$ are subjected to medium pressure liquid chromatography on silica gel using a linear gradient of chloroform (1% NH$_4$OH) to 1:10 (v/v) methanol:chloroform (1% NH$_4$OH). The fractions containing a mixture of AT 2433 $A_1$ and $A_2$ (as determined by tlc) are pooled and evaporated to dryness to give a solid. In a similar fashion, AT 2433 $B_1$ and $B_2$ are purified. The separation of AT 2433 $A_1$ from AT 2433 $A_2$ is effected using medium pressure liquid chromatography on a otcadecylsilane treated silica gel (C-18 silica gel) column using as an eluant 4:3:3: (v/v/v) acetonitrile:methanol: 0.1M ammonium acetate. The eluant is monitored by tlc and fractions containing impure AT 2433 $A_2$ and AT 2433 $A_1$, respectively, are pooled and evaporated to dryness. The impure AT 2433 $A_2$ is purified by repeating the medium pressure liquid chromatography on C-18 silica gel.

AT 2433 $B_1$ is separated from AT 2433 $B_2$ by medium pressure liquid chromatography on C-18 silica gel using as an eluant 4:3:3 (v/v/v) acetonitrile: methanol:ammonium acetate.

The structures of the compounds of this invention, i.e., AT 2433 $A_1$, AT 2433 $A_2$, AT 2433 $B_1$ and AT 2433 $B_2$ are determined by analysis of their infrared, ultraviolet, $^1$H and $^{13}$C nuclear magnetic resonance and mass spectra.

BIOLOGICAL ACTIVITY OF AT 2433 $A_1$, AT 2433 $A_2$, AT 2433 $B_1$ and AT 2433 $B_2$ Antibiotics AT 2433 $A_1$, AT 2433 $A_2$, and AT 2433 $B_1$ and AT 2433 $B_2$ were tested in-vitro to determine anti-bacterial activity against a variety of gram-positive and and gram-negative organisms The in-vitro antibacterial activity tests were performed via conventional agar dilution methods in Muell-Hintom agar (MHA) at pH 7.4.

Antibiotics AT 2433 $A_1$, $A_2$, $B_1$ and $B_2$ were determined to be active gram positive bacteria. All four antibiotic compounds exhibited the greatest antibacterial in-vitro activity against *Sarcina lutea* (ATCC 9341) with AT 2433 $A_1$ and $B_1$ having a Minimum Inhibitory Concentration (MIC) of 0.25 (mcg/mL, MHA, 48 hrs) and with AT 2433 $A_2$ and $B_2$ having MIC's of 1.0 and 4.0, respectively. The four compound were also determined to have in-vitro anti-bacterial activity against *Bacillus subilis* (ATCC 6633), Staphylocci strains *falcium* (ATCC 09790) and *fascalis* (ATCC 29212).

Antibiotic AT 2433 $B_1$ was also determined to have in-vitro activity against the gram-negative bacterium, *E. Coli* SS 1431 with a MIC of 16.0 (mcg/mL, MHA, 48 hrs).

The compounds of this invention designated as AT 2433 $A_1$ and AT 2433 $B_1$ exhibited in-vivo antitumor activity against the transplanted mouse P-388 leukemia.

Anti-tumor activity was determined by the standard National Cancer Institute test which was published in Cancer Chemothr. Rep. 3:1–103, 1972.

In the test, $10^6$ cells (a lethal dose) per mouse of P-388 leukemia are administered interperitoneally on day 0. The test compounds are serially diluted (1:2, 1:4, 1:8, etc.) and each dilution is administered interperitoneally to the mice on days 1, 4 and 7.

The test results summarized in Table VI.

TABLE VI

Effect of AT 2433 $A_1$ and $B_1$ on P-388 Leukemia[1,2]

| Material | Dose, IP[3] (mg/kg/inj) | MST[5] (days) | MST[6,7] (% T/C) | Avg. wt. change, gm on day 5 | Survivors day 5 |
|---|---|---|---|---|---|
| AT 2433 $A_1$ | 16 | Tox[4] | Tox[4] | −3.2 | 2/6 |
| AT 2433 $A_1$ | 8 | 17.5 | 194 | −4.1 | 4/6 |
| AT 2433 $A_1$ | 4 | 14.0 | 156 | −2.3 | 5/6 |
| AT 2433 $A_1$ | 2 | 15.5 | 172 | −2.2 | 6/6 |
| AT 2433 $A_1$ | 1 | 13.5 | 150 | −0.7 | 6/6 |
| AT 2433 $A_1$ | 0.5 | 13.5 | 150 | −0.2 | 6/6 |
| AT 2433 $B_1$ | 16 | 13.0 | 144 | −0.7 | 6/6 |
| AT 2433 $B_1$ | 8 | 12.0 | 133 | −0.3 | 6/6 |
| AT 2433 $B_1$ | 4 | 12.0 | 133 | −0.6 | 6/6 |
| AT 2433 $B_1$ | 2 | 11.0 | 122 | 0.0 | 6/6 |
| AT 2433 $B_1$ | 1 | 10.5 | 117 | 3.0 | 5/5 |
| AT 2433 $B_1$ | 0.5 | 10.0 | 111 | 3.0 | 5/5 |
| Control | 0.56 mL | 9.0 | 100 | +1.6 | 10/10 |

Footnotes to Table VI
[1] Tumor inoculum: $10^6$ ascites cells, ip
[2] Host: CDF$_1$ male mice
[3] Treatment schedule: For AT 2433 $A_1$ and $B_1$, ip. days 1, 4 and 7.
[4] Tox: Toxic, i.e., <4/6 mice alive on day 5
[5] MST: Median survived time in days
[6] % T/C: (MST-Treated/MST-Control) × 100
[7] Criteria: If % T/C >125, the test compound is considered to exhibit significant anti-tumor activity at that dose.

For AT 2433 $A_1$, at the maximum tolerated dose (no day 5 or earlier deaths due to toxicity) of 2 mg/kg given every 3rd day for 3 injections, the increase in life span over controls was 72% (%T/C=172). For AT 2433 $B_1$ the highest dose tested of 16 mg/kg was inhibitory to tumor growth but less effective than AT 2433 $A_1$.

Similar activity is expected for antibiotics AT 2433 A$_2$ and AT 2433 B$_2$.

THERAPEUTIC USE

As mentioned hereinabove, the compounds of this invention represented by formula 1 exhibit antibacterial activity against a variety of gram-positive, and in one case (AT 2433 B$_1$), gram-negative bacteria.

The present invention, therefore provides a method of treating susceptible bacterial infections, which comprises administering to a host, i.e., a warm-blooded mammal, in need of such treatment a compound of this invention represented by formula 1 or a pharmaceutical composition thereof in an amount sufficient to treat such infections.

The compounds of this invention also exhibit antitumor activity against mammalian malignant tumors, e.g., P-388 leukemia in mice.

In another aspect, the present invention also provides a method of treating a mammalian host affected by a malignant tumor, which comprises administering to said host having malignant tumor a therapeutically effective amount of a compound of this invention represented by formula 1 or a pharmaceutical composition thereof.

In yet another aspect, the present invention provides a pharmaceutical composition comprising a compound of this invention represented by formula 1 or a pharmaceutically acceptable salt thereof, in racemic or optically active form and an inert pharmaceutically acceptable carrier or diluent.

Typical suitable pharmaceutically acceptable salts are acid addition salts formed by adding to the compounds of this invention an equivalent of a mineral acid such as HCl, HF, HNO$_3$, H$_2$SO$_4$ or H$_3$PO$_4$ or an organic acid, such as acetic, propionic, oxalic, valeric, oleic, palmitic, stearic, lauric, benzoic, lactic, para-toluene sulfonic, methane sulfonic, citric, maleic, fumaric, succinic and the like.

The pharmaceutical compositions may be made up by combining the compounds of this invention or a pharmaceutically acceptable salt thereof with any suitable, i.e., inert pharmaceutical carrier or diluent and administered orally, parentally or topically in a variety of formulations.

Examples of suitable compositions include solid compositions for oral administration such as tablets, capsules, pills, powders and granules, liquid compositions for oral administration such as solutions, suspensions or emulsions. They may also be manufactureed in the form of sterile solid compositions which can be dissolved in sterile water, physiological saline or some other sterile injectable medium immediately before use.

It will be appreciated that the actual preferred dosages of the compounds of this invention or pharmaceutically acceptable salts thereof will vary according to the particular compound being used, the particular composition formulated, the mode of application and the particular situs, host and disease being treated. Many factors that modify the action of the drug will be taken into account by the attending clinician, e.g. age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by the attending clinician using conventional dosage determination tests.

The following examples illustrate the claimed invention.

GENERAL METHODS

Solvents and Reagents

Solvents used for column chromatography, medium pressure LC and precipitations were not redistilled. Chloroform, carbon tetrachloride and methanol were anhydrous ACS grade. Water refers to in-house deionized water passed through a Millipore 4 housing reagent grade water system (18 megohm Milli-Q-water). Acetonitrile and dimethyl sulfoxide were hplc grade solvents. Tetrahydrofuran was preservative-free Omnisolve hplc grade. Skellysolve B was purchased from Getty Oil and not repurified. Ammonium acetate was Fisher Certified ACS grade. The eluant (normally collected in 50 mL fractions) from the column chromatography was monitored at 405 nm and 435 nm with a ISCO ultraviolet (uv) detector. Parts were by volume.

Thin Layer Chromatography (tlc) was carried out on Whatman LK5DF or LK6DF silica gel plates (20 cm × 20 cm 0.25 mm thick). The plates were developed in Dasaga tlc tanks. The tanks were charged with 200 mL of eluant and allowed to equilibrate prior to plate introduction. Developed, air dried plates were visualized with 366 nm ultraviolet light.

Infrared spectra were measured on a Beckman IR model 4230 instrument. Ultraviolet spectra were measured on a Beckman Acta III UV instrument. $^1$H and $^{13}$C NMR spectra were measured on a Bruker WM 360 instrument at 360 and 90 MHz, respectively. Chemical Ionization mass spectra using CH$_4$ as a reactant gas were measured on a Hewlett-Packard HP 5985B instrument. Field Desorption Low and High Resolution mass spectra were measured on a Varian MAT-731 instrument.

EXAMPLE 1

Fermentation Conditions for Production of Antibiotic AT 2433 Complex

Stock Culture:

Stock cultures of *Actinomadura melliaura* ATCC 39691 were maintained as frozen whole broths.

Inoculum:

A. First Stage: A 5 vol. % inoculum from the thawed stock suspension of *Actinomadura melliaura* (ATCC 39691) was used to inoculate 70 mL of seed Medium A (beef extract, 3.0 g; tryptone, 5.0 g; yeast extract, 5.0 g; cerelose, 1.0 g; potato starch, 24.0 g; CaCO$_3$, 2.0 g; tap H$_2$O, 1000 mL; pH 7.5 with NaOH) in a 300 mL Erlenmeyer flask. The flask was incubated at 30° C. for 48 hrs on a 2 inch stroke gyratory shaker at a speed of 300 rpm.

B. Second Stage: 500 mL of seed Medium A were inoculated with 25 mL (5 vol. %) of the first stage inoculum in two liter Erlenmeyer flasks and incubated in accordance with procedure described for Example 1A.

C. Fermentation: 10 L of fermentation Medium B (yeast extract, 5.0 g; NZ-Amine, 5.0 g; NZ-Amine, 5.0 g; cerelose, 10.0 g; soluble starch, 20.0 g; CaCO$_3$, 4.0 g; tap H$_2$O, 1000 mL; CoCl$_2$(c, 10$^{-3}$M, 1.0 mL) in a 14 L fermentor was inoculated with 70 mL of 5 vol. % inoculum from the second stage. Fermentations were carried out for 96 hr at 30° C. with 350 rpm agitation and air flow of 0.35 VVM.

Production of the antibiotic AT 2433 complex was monitored by whole broth well assays against *Mi-* crococus luteus ATCC 9341 or *Staphylococcus aureus* 209P in neomycin assay agar (BBL).

D. Isolation: 110 L of fermentation broth were extracted with 2×110 L of ethyl acetate. The ethyl acetate extracts were combined and the solvent was evaporated in vacuo to give 32.6 g of crude solid antibiotic complex AT 2433.

EXAMPLE 2

Separation of Antibiotic AT 2433 complex into AT 2433 A($A_1$ and $A_2$) and AT 2433 B($B_1$ and $B_2$).

Liquid-Liquid Partition of Crude Solid Antibiotic AT 2433 complex:

Crude solid antibiotic complex AT 2433 (32.6 g) for Example 1 was dissolved in 200 mL of Skellysolve B and 200 mL of methanol using a Cole-Palmar Model 8845-60 Ultrasonic Cleaner. The solution was transferred to a 1 L separatory funnel and diluted with 22.2 mL of water. The mixture was shaken and the resultant phases allowed to separate. The aqueous methanol (lower phase) was transferred to a second separatory funnel. The aqueous methanol phase was extracted two more times with 200 mL aliquots of Skellysolve B which had been previously saturated with an equal volume of 10% (v/v) water in methanol. The aqueous methanol phase was diluted with 44.4 mL of water and extracted 3 times with 200 mL aliquots of carbon tetrachloride which had previously been saturated with an equal volume of 25% (v/v) water in methanol. The aqueous methanol phase was diluted with 41 mL of water and extracted six times with 200 mL aliquots of chloroform. The chloroform had been previously saturated with an equal volume of 35% (v/v) water in methanol. The chloroform extracts were pooled and evaporated in vacuo to dryness in a rotatory evaporator to yield 5.45 g of residue A, a mixture containing the four compounds AT 2433 $A_1$, $A_2$, $B_1$, and $B_2$.

B. Column Chromatography of Residue A:

The following solvents were equilibrated in a 6 L separatory funnel; 2160 mL of chloroform; 2160 mL of methanol; and 1620 mL of water. The resultant phases were separated. The lower phase was used as the eluant for the column and tlc chromatography.

A 2.0 cm i.d.×100 cm Glenco series 3500 Universal LC Column was slurry packed with 140 g of Woelm silica gel (0.032-0.063 mm) in the above eluant. A sample of 5.45 g of residue A in 10 mL of eluant was drawn into the 15 mL sample loop. The sample loop was connected into the medium pressure LC system. Elution commenced with a flow rate of approximately 21 mL/min collecting the following fractions: fraction 1-180 mL; fraction 2-100 mL; Fraction 3-50 mL; fractions 4 through 33-75 mL each. Aliquots (25 μL) of each fraction were spotted on Whatman LK6DF silica gel tlc plates. The plates were developed with the eluant and viewed with 366 nm ultraviolet light. Fractions 7-14 were pooled and evaporated in vacuo in a rotatory evaporator to yield crude AT 2433 A, a mixture of AT 2433 $A_1$ and $A_2$ (1.2 g). Fractions 14-21 were pooled and evaporated in vacuo in a rotatory evaporator to yield crude AT 2433 B, a mixture of AT 2433 $B_1$ and $B_2$ (1.4 g).

C. Column Chromatography of Crude AT 2433 A:

A 2.0 cm i.d.×30 cm Glenco column was slurry packed with 37 g of Woelm silica gel (0.060-0.200 nm, 70-230 mesh) in chloroform. The top 4 cm of silica gel was removed and added to a solution of crude AT 2433 A (1.7 g) in 200 mL of 2 parts chloroform-1 part methanol. The solvent was evaporated in vacuo in a rotatory evaporator. The resultant bright yellow powder was slurried in chloroform and repacked onto the column. The column was equilibrated by pumping 300 ml of chloroform saturated with ammonium hydroxide (1% by volume conc. ammonium hydroxide-99% chloroform, lower phase). Elution commenced with a 2 L linear gradient of chloroform saturated with ammonium hydroxide (1% by volume conc. ammonium hydroxide added) and 40 fractions were collected at a flow rate of 21 mL/min. The eluant was monitored at 405 nm. Fractions 31-34 were pooled and evaporated to dryness in vacuo in a rotatory evaporator. The residue was dissolved in 50 mL of 2 parts chloroform-1 part methanol. The solution was added very slowly to a rapidly stirring Skellysolve B (1700 mL). The resultant precipitate was collected by filtration to yield 697.5 mg of homogenous AT 2433 A, a mixture of AT 2433 $A_1$ and $A_2$, free from AT 2433 $B_1$ and $B_2$.

D. Column Chromatography of Crude AT 2433 B:

A 2.0 cm i.d.×30 cm Glenco column was slurry packed with 37 g of Woelm silica gel (0.032-0.063 mm) in chloroform. The top 2 cm of silica gel was removed and added to a solution (50 mL) of 500 mg of crude AT 2433 B, a mixture of AT 2433 $B_1$ and $B_2$ in 2 parts chloroform-1 part methanol. The solvent was evaporated in vacuo in a rotatory evaporator. The bright yellow impregnated silica gel was repacked onto the column using a chloroform slurry. The column was equilibrated with chloroform saturated with concentrated ammonium hydroxide (1% by volume). Elution commenced with a 2 L linear gradient of chloroform saturated with ammonium hydroxide (1% by volume of concentrated ammonium hydroxide added) and 16 fractions (approximately 100 mL each) were collected. The eluant was monitored at 405 nm. The following fractions were created after inspection of the chromatogram: fraction 1, 0 to 1218 mL; fraction 2, 1219 mL to 1746 mL; and fraction 3, 1765 mL to 2000 mL. Fraction 2 was evaporated to dryness in vacuo in a rotatory evaporator. The residue was dissolved in 5 mL of 2 parts chloroform-1 part methanol. The solution was added to 1 L of very rapidly stirred Skellysolve B. The resultant precipitate was collected by filtration to yield 454 mg of homogeneous AT 2433 B, a mixture of AT 2433 $B_1$ and $B_2$, free from AT 2433 $A_1$ and $A_2$.

EXAMPLE 3

Resolution of AT 2433 $A_1$ and $A_2$:

A. 2.65 cm i.d.×60 cm Glenco column was slurry packed with Baker C-18 silica gel (octadecylsilane bonded to silica gel) (0.040 mm average particle size) in methanol. The column was connected into the medium pressure LC system and equilibrated with 600 mL of the following eluant: 4 parts acetonitrile, 3 parts methanol, and 3 parts 0.1M ammonium acetate. A sample of 360 mg of AT 2433 A obtained from Example 2C in 1 ml of dimethylsulfoxide was drawn into the sample loop and pumped onto the column with eluant. Elution commenced monitoring the eluant at 405 nm and 435 nm. Approximately 50 ml fractions were collected at a flow rate of approximately 19 mL/min. Based on the elution chromatogram, fractions 12 through 16 were pooled to create fraction 1 and fractions 17 through 24 were pooled to yield fraction 2. The chromatography was repeated 4 times using fresh AT 2433 A (obtained from Example 2C) each time (run 2, 100 mg; run 3, 167 mg; run 4, 160 mg; run 5, 188 mg). Fraction 1 from each of the 5 runs was pooled and extracted with 1000 mL of chloroform. The extract (lower phase) was concentrated to dryness to yield crude AT 2433 $A_2$. Fraction 2 from each run was worked up separately. The pooled fractions were extracted with 500 mL of chloroform. The extract (lower phase) was concentrated to dryness. The residue was dissolved in 2 mL of 2 parts chloroform and 1 part methanol. This solution was added to 500 mL of Skellysolve B with rapid stirring. The resultant precipitate was collected by filtration to yield AT 2433 $A_1$.

B. 1.65 cm i.d.×60 cm Glenco tube was slurry packed with Baker C-18 silica gel in methanol. The column was inserted into the medium pressure LC system and equilabrated with eluant (see above). Crude AT 2433 $A_2$ from Example 3A dissolved in 1 mL of dimethylsulfoxide. The solution was drawn up into the 15 mL sample loop and pumped onto the column. Elution was commenced collecting approximately 50 mL fractions. The eluant was monitored at 405 nm and 435 nm with the ISCO uv detector. Based on the resulting chromatogram, fractions 16 through 28 were pooled. The pooled fractions were extracted with 1000 mL of chloroform. The lower phase (chloroform) was separated and evaporated to dryness in vacuo in a rotatory evaporator. The residue was dissolved in 5 mL of 2 parts chloroform and 1 part methanol. This solution was added to 500 mL of Skellysolve B with rapid stirring. The resultant precipitate was collected by filtration to yield AT 2433 $A_2$.

The following physical and chemical properties of AT 2433 $A_1$ and AT 2433 $A_2$ are listed in Tables VII and VIII, respectively.

TABLE VII

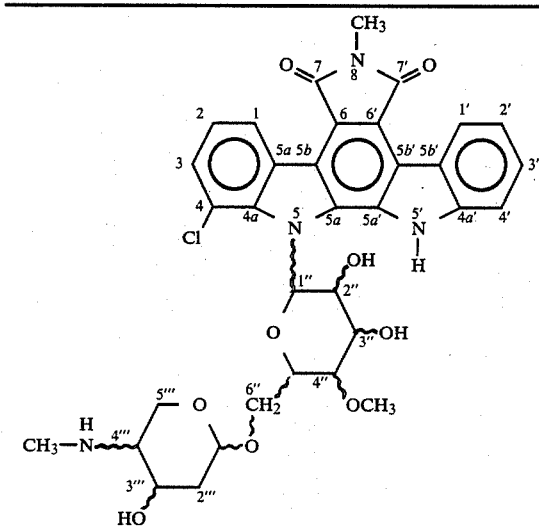

| | AT 2433 $A_1$ |
|---|---|
| Description: | Yellow amorphous solid or fine needle crystals |
| Molecular Formula: | $C_{34}H_{35}ClN_4O_9$ |
| Molecualr Weight: | 679.17 Determined by Chemical Ionization Mass Spectrometry using $CH_4$ as reactant gas. [CI-MS-$CH_4$] |
| Ultraviolet Spectrum: | λmax(c, 0.02290 g/L $CH_3OH$); Observed maxima and absorbitivities (in brackets) = 200 nm(45.5), 235 mn(58.9), 283 nm(50.6), 316 nm(67.2), 395 nm(5.7). |

TABLE VII-continued

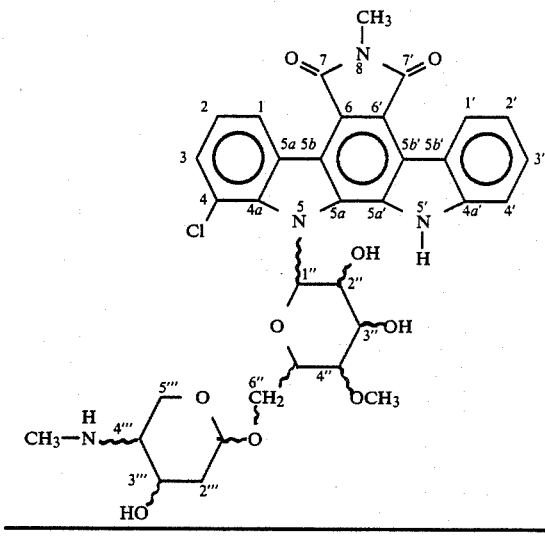

| Infrared Spectrum: | λmax(KBr); 3425, 3362, 2940, 1750, 1696, 1581, 1475, 1462, 1442, 1382, 1335, 1277, 1242, 1194, 1128, 1078, 1052, 768, 759 $cm^{-1}$. |
|---|---|

$^1$H NMR 360 MHz Nuclear Magnetic Resonace Spectrum:

Observed Chemical Shifts and Pattern Description $\delta_H$ (dimethyl sulfoxide-$d_6$):

10.64 (s, 1H, N5'-H), 9.27 (d, 1H, C1-H or C1'-H), 9.18 (d, 1H, C1'-H or C1-H), 7.88 (d, 1H, C4'-H), 7.73 (m, 2H, C3-H and C3'-H), 7.49 (m, 2H, C2-H and C2'H), 6.91 (d, 1H, C1''-H), 5.48 (brs, 1H, C3''-OH), 5.13 (m, 1H, C1'''-H), 5.06 (brs, 1H, C2''-OH), 4.81 (brs, 1H, C3'''-OH), 4.21 (brd, 1H, C6a''-H), 4.08 (brd, 1H, C5''-H), 3.99 (dd, 1H, C6b''-H), 3.77 (dd, 1H, C3'''-H), 3.60–3.70 (m, 6H, C2''-H, C3''-H, C4''-H, C5a''-H, C5b'''-H), 3.68 (s, 3H, C4-H''-O$CH_3$), 3.40 (m, 1H, C4'''-H overlaps with $H_2O$), 3.25 (s, 3H, N8-$CH_3$), 2.30 (m, 2H, C4'''-NH, C2'''-H), 2.22 (s, 3H, C4'''-N$CH_3$), 1.78 (m, 1H, C2b'''-H).

$^{13}$C NMR 90 MHz Nuclear Magnetic Resonance Spectrum

Observed Chemical Shifts and Assigments $\delta_C$ (dimethyl sulfoxide-$d_6$):

| PPM | Assignment | PPM | Assignment |
|---|---|---|---|
| 169.0 | C7 | 117.6 | C5b |
| 169.0 | C7' | 116.4 | C4 |
| 140.2 | C4a | 112.1 | C4' |
| 138.1 | C4a' | 99.0 | C1''' |
| 130.0 | C5a | 84.7 | C1'' |
| 129.7 | C3' | 78.8 | C3'' |
| 129.5 | C5a' | 78.1 | C4'' |
| 127.8 | C3 | 77.5 | C5'' |
| 125.3 | C5c | 72.2 | C2'' |
| 124.6 | C1' | 66.5 | C3''' |
| 123.4 | C1 | 66.0 | C6'' |
| 122.4 | C2 | 61.8 | C5''' |
| 121.4 | C5c' | 61.7 | C4''' |
| 121.3 | C6 | 60.1 | C4''-O$CH_3$ |
| 121.0 | C2' | 37.0 | C2''' |
| 119.2 | C6' | 33.9 | C4'''-N$CH_3$ |
| 118.4 | C5b' | 23.6 | N8-$CH_3$ |

Mass Spectrum (CI-MS-$CH_4$): M/Z = 679[M + 1]$^+$

TABLE VIII

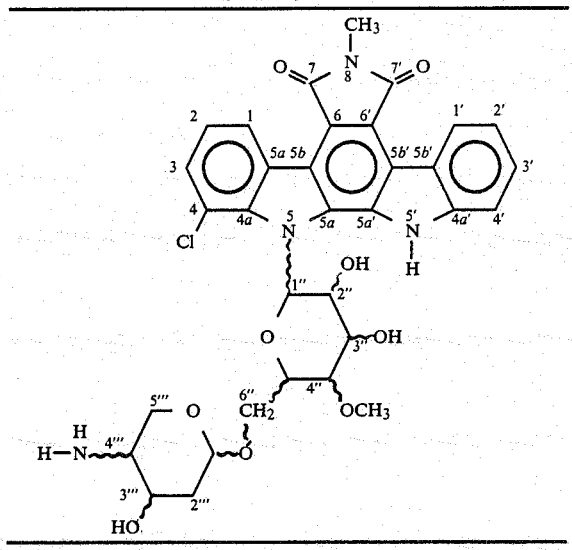

| | AT 2433 A$_2$ |
|---|---|
| Description: | Yellow amorphous solid |
| Molecular Formula: | C$_{33}$H$_{33}$ClN$_4$O$_9$ |
| Molecular Weight: | 665.10 |
| Ultraviolet Spectrum: | λmax(c, 0.0158 g/L CH$_3$OH); Observed maxima and absorbitivities (in brackets) = 198 nm(45.9), 233.5 mn(58.2), 286 nm (50.6), 314 nm(66.1), 394 nm(5.2). |
| Infrared Spectrum: | λmax(KBr); 3420, 3355, 2930, 1745, 1691, 1575, 1472, 1458, 1438, 1380, 1330, 1278, 1240, 1140, 1120, 1080, 1045, 765, 755 cm$^{-1}$. |

$^1$H NMR 360 MHz Nuclear Magnetic Resonace Spectrum:
Observed Chemical Shifts and Pattern Description δ$_H$ (dimethyl sulfoxide-d$_6$):

10.64 (s, 1H, N5'-H), 9.27 (d, 1H, C1-H or C1'-H), 9.18 (d, 1H, C1'-H or C1-H), 7.88 (d, 1H, C4'-H), 7.33 (m, 2H, C3-H and C3'-H), 7.49 (m, 2H, C2-H and C2'-H), 6.91, (d, 1H, C1"-H), 5.48 (brs, 1H, C3"-OH), 5.14 (m, 1H, C1'''-H), 5.06 (brs, 1H, C2"-OH), 4.81 (brs, 1H, C3'''-OH) 4.21 (brd, 1H, C6a"-H), 4.08 (brd, 1H, C5"-H), 3.99 (dd, 1H, C6b"-H), 3.68 8s, 3H, C4"-OCH$_3$), 3.72–3.30 (m, 7H, C2"-H, C3"-H, C4"-H, C3'''-H, C4'''-H, C5a'''-H, C5b'''-H overlaps with H$_2$O), 3.25 (s, 3H, N8-CH$_3$), 2.55 (m, 2H, C4'''-NH$_2$), 2.32 (m, 1H, C2a'''-H), 1.73 (m, 1H, C2b'''-H).

| Mass Spectra: | Field Desorption Low and High Resolution Measurements: |
|---|---|
| FD-LR-MS: | m/z 664 [M]$^+$ |
| | m/z 687 [M + Na]$^+$ |
| FD-HR-MS: | m/z 664.1795 observed, |
| | 664.1936 expected for C$_{33}$H$_{33}$ClN$_4$O$_9$ |

EXAMPLE 4

Resolution of AT 2433 B$_1$ and B$_2$:

A 2.65 cm (i.d.)×60 cm Glenco column was slurry packed with Baker C-18 silica gel (0.040 mm average particle size) in methanol. The column was inserted into the medium pressure LC system and equilibrated with 600 mL of the following eluant: 3 parts of acetonitrile, 3 parts of methanol, and 4 parts of 0.1M ammonium acetate. A sample of 360 mg of AT 2433 B obtained from Example 2D in 2 mL of dimethylsulfoxide was drawn into the sample loop and pumped onto the column with eluant. Elution was commenced monitoring the eluant at 405 nm and 435 nm with the ISCO uv detector and collecting 50 mL fractions. Aliquots (5 μL) of fractions 14 through 19 were assayed by hplc using a μ-Bondapak C-18 column and an eluant of 4 parts of acetonitrile, 3 parts of methanol and 3 parts of 0.1M ammonium acetate. Fractions 14 through 16 were pooled and extracted with 500 mL of chloroform. The lower phase (chloroform) was separated and concentrated to dryness to yield AT 2433 B$_2$. Fractions 17 through 24 were pooled and extracted with 500 mL of chloroform. The lower phase (chloroform) was separated and concentrated to dryness to yield crude AT 2433 B$_1$. The crude AT 2433 B$_1$ was rechromatographed and isolated exactly as described above to yield approximately 180 mg of pure AT 2433 B$_1$.

The physical and chemical properties of AT 2433 B$_1$ and B$_2$ are listed in Tables IX and X respectively.

TABLE IX

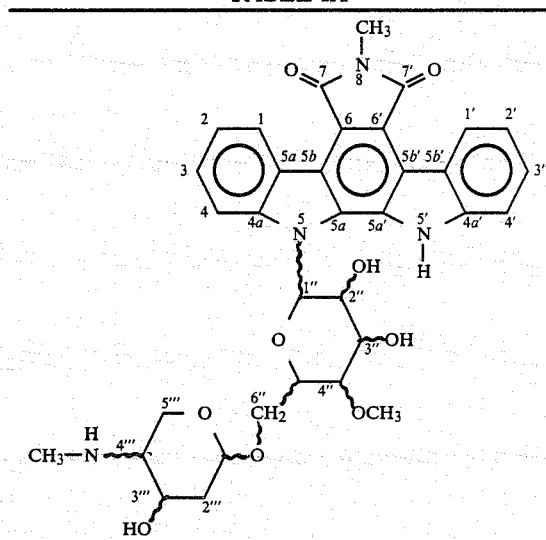

| | AT 2433 B$_1$ | |
|---|---|---|
| Description: | Yellow amorphous solid | |
| Molecular Formula: | C$_{34}$H$_{36}$N$_4$O$_9$ | Determined by |
| Molecular Weight: | 644.68 | Field Desorption Low and High Resolution Mass Spectrometry and CI-MS-CH$_4$ |
| Ultraviolet Spectrum: | λmax(c, 0.0222 g/L CH$_3$OH); Observed maxima and absorbitivities (in brackets) = 202 nm(45.0), 234 mn(64.1), 284 nm(52.2), 316 nm(72.9), 400 nm(6.3). | |
| Infrared Spectrum: | λmax(KBr); 3363, 2940, 1750, 1692, 1575, 1475, 1460, 1435, 1380, 1332, 1240, 1185, 1105, 1010, 750 cm$^{-1}$. | |

$^1$H NMR 360 MHz Nuclear Magnetic Resonace Spectrum:
Observed Chemical Shifts and Pattern Description δ$_H$ (dimethyl sulfoxide-d$_6$):

10.50 (brs, 1H, N5'-H), 9.32 (d, 1H, C1-H or C1'-H), 9.21 (d, 1H, C1'-H or C1-H), 8.14 (d, 1H, C4-H), 7.86 (d, 1H, C4'-H), 7.68 (m, 2H, C3-H and C3'-H), 7.48 (m, 2H, C2-H and C2'-H), 6.44, (d, 1H, C1'-H), 5.6–4.6 (br. m, 4H, C3"-OH, C1'''-H, C2"-OH, C3"-OH), 4.3–3.2 (m, 10H, C2"-H, C3"-H, C4"-H, C5"-H, C6a"-H, C6b"-H, C3'''-H, C4'''-H, C5a'''-H, C5b'''-H), 3.68 (s, 3H, C4"-OCH$_3$), 3.25 (s, 3H, N8-CH$_3$), 2.35 (m, 1H, C4'''-NH), 2.30 (s, 3H, C4'''-NCH$_3$), 2.03 (m, 1H, C2a'''-H), 1.60 (m, 1H, C2b'''-H).

$^{13}$C NMR 90 MHz Nuclear Magnetic Resonance Spectrum:
δ$_c$ (dimethyl sulfoxide-d$_6$)

Observed Chemical Shifts (PPM):
169.6, 169.5, 140.5, 139.5, 127.4, 127.2, 127.0, 126,7, 124.5, 124.3, 124.2, 120.9, 120.3, 114.7, 111.7, 97.8, 86.5, 79.1, 76.2, 76.0, 71.1, 66.3, 65.7, 61.9, 60.3, 60.0, 38.0, 23.6.

| Mass Spectra: | Chemical Ionization-CH$_4$: m/z = 645, [M + 1]$^+$ |
|---|---|
| | Field Desorption Low and High |

TABLE IX-continued

Resolution Measurments
LR-MS: m/z = 644, [M]+
m/z = 667, [M + Na]+
HR-MS: m/z = 644.2401 observed,
644.2476 expected for C₃₄H₃₆N₄O₉

TABLE X

| | |
|---|---|
| | AT 2433 B₂ |
| Description: | Yellow amorphous solid |
| Molecular Formula: | C₃₃H₃₄N₄O₉  Determined by Field |
| Molecular Weight: | 630.65  Desorption Low and High Resolution Mass Spectrometry |
| Ultraviolet Spectrum: | λmax(c, 0.0184 g/L CH₃OH); Observed maxima and absorbitivities (in brackets) = 201 nm(48.9), 233 mn(65.2), 282 nm(53.0), 315 nm(74.5), 400 nm(6.3). |
| Infrared Spectrum: | λmax(KBr); 3500sh, 3365, 2940, 1750, 1692, 1578, 1478, 1462, 1437, 1381, 1332, 1277, 1241, 1115, 1085, 1055, 1012, 995, 750 cm⁻¹. |

¹H NMR 360 MHz Nuclear Magnetic Resonace Spectrum:
Observed Chemical Shifts (PPM) and Pattern Description δ$_H$
(dimethyl sulfoxide-d₆):
10.50 (brs, 1H, N5'-H), 9.32 (d, 1H, C1-H or C1'-H), 9.21 (d, 1H, C1'-H or C1-H), 8.14 (d, 1H, C4''-H), 7.86 (d, 1H, C4'-H), 7.68 (m, 2H, C3-H and C3'-H), 7.48 (m, 2H, C2-H and C2'-H), 6.44 (d, 1H, C1'-H), 5.6-4.6 (br. m, C3''-O$\underline{H}$, C1'''-H, C2''-O$\underline{H}$, C3''-O$\underline{H}$), 4.3-3.2 (m, 10H, C2''-H, C3''-H, C4''-H, C5''-H, C6a''-H, C6b''-H, C3'''-H, C4'''-H, C5a'''-H', C5b'''-H), 3.68 (s, 3H, C4''-OC$\underline{H}_3$), 3.25 (s, 3H, N8-C$\underline{H}_3$), 2.55 (m, 2H, C4'''-N$\underline{H}_2$), 2.03 (m, 1H, C2a'''-H), 1.60 (m, 1H, C2b'''-H).

| | |
|---|---|
| Mass Spectra: | Field Desorption Low and High Resolution Measurements: |
| LR-MS: | m/z = 630 [M]+ |
| | m/z = 653 [M + Na]+ |
| HR-MS: | m/z = 630.2224 observed, 630.2316 expected for C₃₃H₃₄N₄O₉ |

What is claimed is:

1. A compound represented by the formula 1:

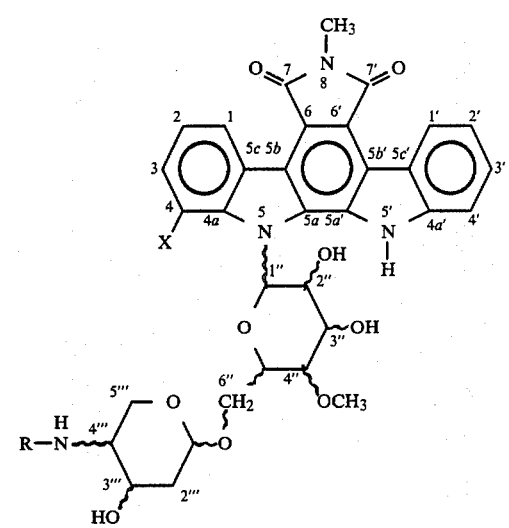

wherein X is H or Cl; and R is H or CH₃; and wavy lines in formula 1 represent bonds to two six-membered sugar rings and signify that substituents attached to each of the two six-membered sugar rings may be in any of the possible stereochemical configurations; or, a pharmaceutically acceptable salt thereof.

2. The compound of claim 1 wherein X is Cl and R is CH₃.

3. The compound of claim 1 wherein X is Cl and R is H.

4. The compound of claim 1 wherein X is H and R is CH₃.

5. The compound of claim 1 wherein X and R are each H.

6. A pharmaceutical composition comprising an antibacterially effective amount of a compound represented by formula 1:

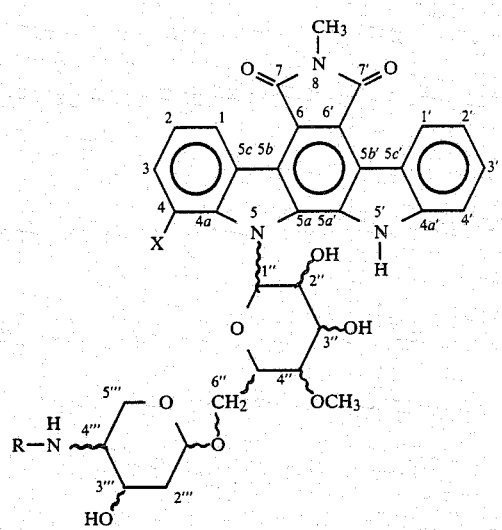

wherein X is H or Cl and wherein R₁ is H or CH₃ and wavy lines in formula 1 represent bonds to two six-membered sugar rings and signify that substituents attached to each of the two six-membered sugar rings may be in any of the possible stereochemical configurations; or, a pharmaceutically acceptable salt thereof; and, an inert pharmaceutically acceptable carrier or diluent.

7. A method of treating susceptible bacterial infections which comprises administering to a host in need of such treatment a compound represented by formula 1:

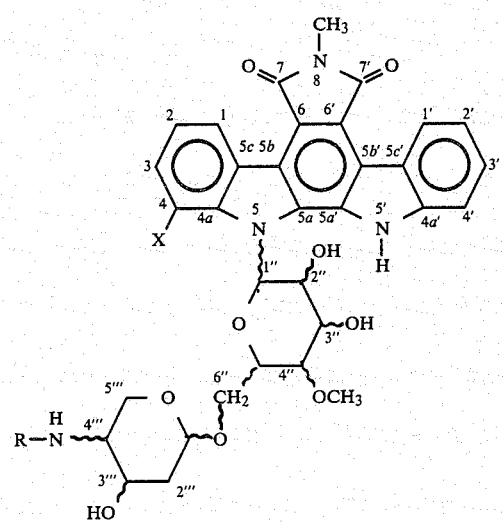

wherein X is H or Cl; and R is H or CH₃; and wavy lines in formula 1 represent bonds to two six-membered sugar rings and signify that substituents to each of the two six-membered sugar rings may be in any of the possible stereochemical configurations; or a pharmaceutical composition thereof in an amount sufficient to treat such infections.

8. The method according to claim 7 wherein the route of administration is oral.

9. The method according to claim 7 wherein the route of administration is topical.

10. The method according to claim 7 wherein the route of administration is parenteral.

11. Antibiotic AT 2433 complex comprising the four compounds represented by the formula 1:

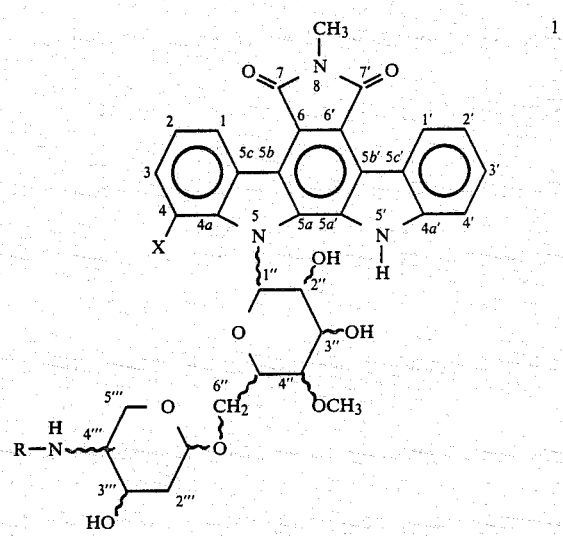

wherein X is H or Cl; and R is H or CH₃; and wherein wavy lines in formula 1 represent bonds to two six-membered sugar rings and signify that substituents to each of the two six-membered sugar rings may be in any of the possible stereochemical configurations.

12. A mixture comprising a compound of formula 1 of claim 1 wherein X is Cl and R is CH₃ which is AT 2433A₁, and a compound of formula 1 of claim 1 wherein X is Cl and R is H which is AT 2433A₂, wherein wavy lines in formula 1 represent bonds to two six-membered sugar rings and signify that substituents to each of the two six-membered sugar rings may be in any of the possible stereochemical configurations.

13. A mixture comprising a compound of formula 1 of claim 1 wherein X is H and R is CH₃ which is AT 2433B₁, and a compound of formula 1 of claim 1 wherein X is H and R is H which is AT 2433B₂, wherein wavy lines in formula 1 represent bonds to two six-membered sugar rings and signify that substituents attached to each of the two six-membered sugar rings may be in any of the possible stereochemical configurations.

* * * * *